United States Patent
Eisele

(10) Patent No.: US 7,718,205 B2
(45) Date of Patent: May 18, 2010

(54) PROCESS FOR PREPARATION OF CALCIUM-D-PANTOTHENATE

(75) Inventor: Frank Eisele, Basel (CH)

(73) Assignee: DSM IP Assets B.V., Heerlen (NL)

( * ) Notice: Subject to any disclaimer, the term of this patent is extended or adjusted under 35 U.S.C. 154(b) by 787 days.

(21) Appl. No.: 11/587,648

(22) PCT Filed: Apr. 18, 2005

(86) PCT No.: PCT/EP2005/004067

§ 371 (c)(1),
(2), (4) Date: Oct. 26, 2006

(87) PCT Pub. No.: WO2005/103274

PCT Pub. Date: Nov. 3, 2005

(65) Prior Publication Data

US 2008/0026107 A1    Jan. 31, 2008

(30) Foreign Application Priority Data

Apr. 26, 2004   (EP) .................................. 04009815

(51) Int. Cl.
*A23L 1/30* (2006.01)
*C12P 13/04* (2006.01)

(52) U.S. Cl. .................. 426/72; 426/271; 426/807; 435/106

(58) Field of Classification Search ............. 426/72, 426/271, 807, 648; 435/106
See application file for complete search history.

(56) References Cited

U.S. PATENT DOCUMENTS

2004/0077057 A1 * 4/2004 Beck et al. ............. 435/106

FOREIGN PATENT DOCUMENTS

JP        05023191 A  *  2/1993

\* cited by examiner

*Primary Examiner*—C. Sayala
(74) *Attorney, Agent, or Firm*—Nixon & Vanderhye P.C.

(57) ABSTRACT

The invention relates to an improved process for the preparation of calcium-D-pantothenate from fermentation broths comprising eluting D-pantothenic acid from a strongly basic anion exchange resin with a weak organic acid and neutralising the eluate with a basic calcium salt.

12 Claims, No Drawings

PROCESS FOR PREPARATION OF CALCIUM-D-PANTOTHENATE

This application is the US national phase of international application PCT/EP2005/004067 filed 18 Apr. 2005, which designated the U.S. and claimed priority of EP 04009815.4 filed 26 Apr. 2004, the entire contents of each of which are hereby incorporated by reference.

The present invention relates to a procedure for the preparation of calcium-D-pantothenate and to compositions based thereon suitable as animal feed supplements.

Calcium-D-pantothenate is the commercially most important product form of D-pantothenic acid. Compared to the pantothenic acid itself and monovalent D-pantothenates calcium-D-pantothenate has the advantage of higher stability and is less hygroscopic. D-Pantothenic acid or vitamin B5 is a member of the vitamin B complex and is a natural requirement for mammals, including livestock and humans. In cells, pantothenic acid is used primarily for the biosynthesis of co-enzyme A (CoA) and the acyl carrier protein (ACP). These co-enzymes are essential to all cells, participating in over 100 different intermediary reactions in cellular metabolism.

About 6000 tons of D-pantothenic acid and its salts were produced in 2001, of which about 80% were used as animal feed additives. It is also used for pharmaceutical, health care and food products. The conventional chemical synthesis of D-pantothenate (only the D-enantiomer is biologically active) from D-pantolactone and β-alaninate requires an optical resolution step of racemic intermediates to obtain the desired D-enantiomer and is therefore hampered by relatively high production costs.

In order to overcome this drawback and to improve the D-pantothenate production process methods of direct microbial synthesis (e.g. from glucose to pantothenate) have been the subject of intensive research and have been developed in recent years.

Meanwhile several fermentation processes for the microbial preparation of D-pantothenates (i.e. D-pantothenic acid and its salts) have been described and are known, e.g., from EP 0 590 857, WO 96/33283, WO 97/10340, EP 1 001 027, EP 1 006 192, EP 1 006 193, WO 01/21772 and others. Some of the processes use microorganisms which have been transformed and genetically manipulated in a highly sophisticated way in order to achieve high yields of D-pantothenate in the fermentation broth.

On the other hand the microbially produced D-pantothenates have to be isolated, purified and have to be converted to the desired product form, viz. calcium-D-pantothenate. Therefore, a variety of downstream processes have been developed and have been published including process steps like filtration, crystallization, the use of ion selective membranes, charcoal adsorption, cation exchange, anion exchange with subsequent neutralization and concentration or drying until formulation.

WO 02/066665 describes a process for the preparation of D-pantothenic acid and/or its salts by a transformant microorganism with a deregulated pantothenic acid (pan) and/or isoleucine/valine (ilv) biosynthesis in which the pantothenic acid from the fermentation broth is fixed by an anion exchange resin, eluted with inter alia an aqueous solution of hydrochloric acid and the free pantothenic acid obtained in the eluate is converted into a calcium and/or magnesium salt by addition of a calcium and/or magnesium base. The product thus obtained is especially useful as animal feed supplement.

The process of the present invention provides a downstream process, that is carried out after the microbial production of D-panothenic acid and/or its salts and that uses anion exchange resins, however, under conditions different from those described in WO 02/066665. This downstream process provides feed grade material of calcium-D-pantothenate in higher purity and/or more economically than other downstream processes known to date. In more detail, the present invention relates to a process for the preparation of calcium-D-pantothenate comprising isolating and purifying it from a fermentation broth of a pantothenic acid producing microorganism which process is characterized by the steps of (a) eluting-D-pantothenic acid from a strongly basic anion exchange resin with an aqueous solution of a weak organic acid,
(b) neutralizing the eluate by the addition of a basic calcium salt and
(c) transferring the solution into a free-flowing product capable of being used as animal feed supplement.

The invention also relates to compositions suitable as animal feed supplements on the basis of calcium-D-pantothenate which can be obtained by the above process.

While the essential step of the present invention is the elution of D-pantothenic acid from the strongly basic anion exchange resin with an aqueous solution of a weak organic acid, the process in specific embodiments may in addition comprise steps commonly used in such downstream processes, in which, e.g., all or only some of the biomass is removed from the fermentation broth before the anion exchange step, the eluate is concentrated prior to neutralization or decolorized at any stage of the process and, finally, formulated.

While by elution of D-pantothenic acid from an anion exchange resin with a strong inorganic acid like hydrochloric acid, as described in WO 02/066665, all other anions bound to the resin are also eluted, the process of the present invention provides a more selective elution of D-pantothenic acid since weaker organic acids, e.g., carboxylic acids, preferably acetic acid, are used. The organic acid is used more or less diluted with water at concentrations of 1-99% (w/w), preferably of 5-50%, more preferably of 8-30% and most preferably of 10-20%. Despite the use of a weaker acid, the removal of D-pantothenate from the strongly basic anion exchange resin is quantitative. Compared to diluted hydrochloric acid (about 5%), the same volume of diluted acetic acid is sufficient to achieve complete elution of D-pantothenic acid.

Thus, the process of the present invention comprises several benefits when compared with elutions using strong inorganic acids. The use of weaker organic acids gives a more selective removal of D-pantothenic acid from the resin. In contrast to hydrochloric acid, the application of acetic acid avoids the elution of inorganic anions such as sulfate or phosphate to a large extent. Thus, the amount of these anions in the final product is reduced by this new technique to a level of <2%, preferably <1%, more preferably <0.5% and most preferably <0.1%. In addition, a product with extremely minimized chloride content is delivered using this new invention. In contrast to large amounts of chloride in products obtained by elution with hydrochloric acid, the chloride content is reduced to <2%, preferably <1%, more preferably <0.5% and most preferably <0.1% by the application of organic carboxylic acids. From a technical point of view, a major benefit of acetic acid is its lower corrosive behavior compared to hydrochloric acid. To this end, the cost of the downstream procedure can be significantly reduced, because cheaper, less stable materials are sufficient for the construction of the plant.

A further benefit of the invention results from step (b) of the present process, the neutralization of the eluate. In this step, the eluate containing D-pantothenic acid is neutralized to a pH of 4-10, preferably 5-9, more preferably 6-8 and most preferably 6.5-7.5 by a basic calcium salt, especially calcium hydroxide or calcium carbonate. These two salts are favored because no additional anionic side product is added in this step. Neutralization with basic salts having other cations than calcium would not lead directly to the preferred calcium D-pantothenate. The basic calcium salts are added as solids or, more favorably, as aqueous suspensions with contents of 2-50%, more preferably 15-45% and most preferably 20-40% of the basic calcium salt. The addition of suspension allows for a better pH control in this step. As mentioned above, elution with hydrochloric acid does not separate the D-pantothenate from inorganic anions like sulfate of phosphate. Since these anions form hardly soluble calcium salts, suspensions would be obtained in the neutralization step. In contrast, the present invention provides a clear solution after the addition of calcium hydroxide to the eluate. Thus, the neutralized solution can be directly submitted to a drying or formulation step without any additional filtration step.

The fermentation process by which the D-pantothenate containing broth is obtained can be conducted according to any method know in the art. Thus, the process can be conducted batch wise, fed-batch wise, repeated-fed-batch wise or continuously using well-known culture media comprising carbon sources, nitrogen sources and inorganic anions, e.g., chlorides, sulfates or phosphates. For the neutralization of the D-pantothenic acid in the fermentation broth the well-known buffer systems are used, e.g., phosphate buffers with NaOH, KOH or $NH_4OH$.

All D-pantothenate producing microorganisms can be used including fungi, yeasts and bacteria such as, e.g., represented by the genera *Saccharomyces, Corynebacterium, Escherichia* and *Bacillus* and described in more detail in the references cited above, e.g., WO 02/066665. Preferred microorganisms are meanwhile those which have been transformed or their pathways have been genetically manipulated (deregulated) in a way that D-pantothenate is overproduced. Several methods how this can be done are well-known by enhancing expression of genes in the D-pantothenate pathways and/or suppressing the expression of genes involved in side-pathways.

Depending upon the microorganism used and the fermentation conditions the fermentation broth will contain D-pantothenate in concentrations of at least 25 g/L, preferably of at least 50 g/L, more preferably of at least 80 g/L and most preferably of at least 100 g/L.

All known and commercially available strongly basic anion exchange resins can be used in the process of the present invention. This includes all strongly basic resins (for example those having quaternized ammonium residues as functional groups), such as Lewatits, Amberlites, Duolite, Dowex and Diaion resins from the following companies, respectively: Bayer, Rohm & Haas, Dow Chemicals, and Mitsubishi Chemicals Corp. The anion exchange resin binds D-pantothenates and other anions while all other components such as cations and neutral compounds pass through and can be discarded. After washing with water the D-pantothenate is then eluted selectively with an aqueous solution of a weak organic acid, preferably acetic acid in a preferred concentration of 10-20%.

The eluate is then adjusted to a pH of 4-10, preferably 5-9, more preferably 6-8 and most preferably 6.5-7.5 by addition of calcium hydroxide or carbonate. In accordance with the present invention an aqueous solution or suspension of 2-55% (w/w) preferably 10-50% and more preferably 20-40% of calcium hydroxide or of 2-65% (w/w), preferably 10-50% and most preferably 20-40% of calcium carbonate is added to the eluate.

In accordance with step (c) of the process of the present invention the neutralized eluate from the anion exchange resin is transferred into a free flowing product which can directly be used as an animal feed supplement according to methods known in the art, e.g. by drying with or without prior concentration and, if desired, formulation using methods well-known in the art (see, e.g. Ullmann's Encyclopedia of Industrial Chemistry, $6^{th}$ edition, 1999) preferably by spray drying or spray granulation. After the drying step, a yellowish product is obtained with a pantothenate content of >20%, preferably >40%, more preferably >65% and most preferably >90% with a calcium content compared to monovalent cations of >90%, preferably >92% more preferably >96% and most preferably >99%. In this product the amount of inorganic anions like chloride, sulfate, phosphate is minimized to <2%, preferably <1%, more preferably <0.5% and most preferably <0.1%.

The process of the present invention can be varied by a single or several additional conventional process steps before step (a), between steps (a)-(c) or even after step (c) if desired. Thus, the solutions, suspensions or products of process steps (a)-(c) can be sterilized by, e.g., heating, filtration or radiation.

If a major amount of acetic acid is present in the eluate, it can be removed right after the elution step (a) by distillation at moderate temperature and low pressure. Because of the low corrosive behaviour of acetic acid compared to strong mineral acids there is no need for special equipment but cheap materials for the distillation equipment can be used. Acetic acid can also be minimized in the eluate using a special set-up of several columns known to a person skilled in the art resulting in acetate levels in the eluate of <2%, preferably <1%, more preferably <0.5% and most preferably <0.1%.

Before the fermentation broth is sent over the anion exchange resin the biomass is suitably lysed and/or killed and/or more or less separated from the broth. This can be effected by methods known in the art. Especially if a product with a high D-pantothenate content is desired, separation of the biomass is effected by methods such as, decantation, filtration and centrifugation, if desired with previous addition of a commercially available flocculant. If no or only partial separation of the biomass is desired, the broth with the biomass is advantageously sent through the anion exchange column from bottom to top, viz. against gravity.

Finally, another modification of the present process may involve a charcoal treatment of one of the solutions if a less colored product, in the extreme a white product is desired. This charcoal treatment is preferably carried out right after fermentation, more preferably after the removal of biomass from the fermentation broth. Most preferred is the charcoal treatment after the neutralization step (b). For this operation all commercially available powdered or granulated charcoal products can be applied.

The present invention is illustrated in more detail by the following examples:

EXAMPLE 1

Fermentation of *B. subtilis*

The fermentation was carried out in a stirred and aerated 2000 L pilot fermenter.

The initial fermentation medium was sterilised in the fermenter at 121° C. for 30 minutes, the composition is described in Table 1.

TABLE 1

Composition of the initial fermentation medium

| Component | Concentration [g/L] |
|---|---|
| yeast extract | 12.0 |
| sodium glutamate | 0.83 |
| $KH_2PO_4$ | 4.71 |
| $K_2HPO_4$ | 4.71 |
| $Na_2HPO_4$ | 4.09 |
| $NH_4Cl$ | 0.23 |
| $(NH_4)_2SO_4$ | 1.41 |
| antifoam Clerol FBA 5057 | 0.2 |

After the sterilisation the components shown in Table 2 were autoclaved separately and added aseptically to the fermenter.

TABLE 2

Components added after sterilisation of initial medium

| Component | Concentration [g/L] |
|---|---|
| glucose | 24.8 |
| $MnSO_4 \cdot H_2O$ | 0.014 |
| $CoCl_2 \cdot 6H_2O$ | 0.004 |
| $(NH_4)_6Mo_7O_{24} \cdot 4H_2O$ | 0.0015 |
| $AlCl_3 \cdot 6H_2O$ | 0.001 |
| $CuCl_2 \cdot 2H_2O$ | 0.00075 |
| $MgSO_4 \cdot 7H_2O$ | 1 |
| $ZnSO_4 \cdot 7H_2O$ | 0.004 |
| $CaCl_2 \cdot 2H_2O$ | 0.0625 |
| $FeSO_4 \cdot 7H_2O$ | 0.042 |

500 L of the medium were inoculated with 25 L of a preculture of a pantothenate overproducing *B. subtilis* strain in which the panBCD operon and the panE gene are overexpressed using a SP01 phage promoter (as described, e.g., in WO 01/21772) with an optical density (OD) of 10.7. The fermentation temperature was 39° C., the used airflow was 700 L/min. A pH of pH 6.85 was maintained by adding gaseous ammonia. By stirrer speed control the dissolved oxygen concentration (DO) remained greater than 15%. The formation of foam was prevented by addition of antifoam Clerol FBA 5057.

The fermentation was carried out as glucose-limited fed-batch fermentation. Over a period of 43 hours 182 L of the feed solution (Table 3) was added to the fermenter.

TABLE 3

Composition of the feed solution

| Component | Concentration [g/L] |
|---|---|
| glucose | 745.5 |
| $MgSO_4 \cdot 7H_2O$ | 2 |
| $MnSO_4 \cdot H_2O$ | 0.015 |
| $ZnSO_4 \cdot 7H_2O$ | 0.004 |
| antifoam Clerol FBA 5057 | 0.003 |

After 48 hours of fermentation the broth was pasteurised at 70° C. for 30 minutes. The concentration of pantothenate in the pasteurised fermentation broth was 32 g/L.

EXAMPLE 2

Amberlite IRA 900; Elution with 10% Acetic Acid

The strongly basic anion exchange resin Amberlite IRA 900 (600 mL) was loaded with 758 mL of the pasteurized and ultrafiltrated bio-broth obtained according to Example 1. The flow rate was regulated to 1 L/h. Using the same flow rate, the column was washed with 1168 mL of demineralized water. Then the pantothenate was eluted with a flow rate of 1 L/h using 2000 mL of acetic acid (10%). 1898 mL of eluate were collected. The column was regenerated with demineralized water (975 mL), 4% aqueous NaOH solution (1639 mL) and again demineralized water (1000 mL).

The eluate was concentrated on a rotary evaporator at reduced pressure and temperatures from 50-70° C.

The concentrated crude product was diluted with water (1:1) and then 5.22 g of Ca(OH) (as a 5% suspension in water) were added to adjust the pH value to 7. The solution was concentrated and dried on a rotary evaporator. 53.60 g of free-flowing yellow product were obtained consisting of 37.1% (w/w) D-pantothenate, <0.1% chloride, <0.1% sulfate and <0.01% phosphate. Cations included 13.6% calcium (97% of all cations detected), 0.2% sodium, <0.1% ammonium, <0.1% potassium and <0.1% magnesium.

EXAMPLE 3

Amberlite IRA 958; Elution with 10% Acetic Acid

The strongly basic anion exchange resin Amberlite IRA 958 (600 mL) was loaded with 1068 mL of the pasteurized and ultrafiltrated bio-broth obtained according to Example 1. The flow rate was regulated to 1 L/h. Using the same flow rate, the column was washed with 617 mL of demineralized water. Then the pantothenate was eluted with a flow rate of 1 L/h using 1079 mL of acetic acid (10%). 1179 mL of eluate were collected. The column was regenerated with demineralized water (711 mL), 4% aqueous NaOH solution (747 mL) and again demineralized water (1000 mL).

The eluate was split in two portions, first portion: 601 g, second portion: 567 g.

Portion 1 was concentrated on a rotary evaporator at reduced pressure and a temperature in the range of 50-70° C. The concentrated crude product was diluted with water (1:1) and then 8 g of $Ca(OH)_2$ (as a 25% suspension in water) were added to adjust the pH value to 7. The solution was concentrated and dried on a rotary evaporator. 36.0 g of free-flowing yellow product were obtained consisting of 42.8% (w/w) D-pantothenate, <0.1% chloride, 0.50% sulfate and <0.01% phosphate. Cations included 11.2% calcium (97% of all cations detected), 0.2% sodium, <0.1% ammonium, <0.1% potassium and <0.1% magnesium.

Portion 2 was directly submitted to the neutralization step. 21.7 g of $Ca(OH)_2$ (as a 25% suspension in water) were added to adjust the pH value to 7. The solution was concentrated and dried on a rotary evaporator. 61.1 g of free-flowing yellow product were obtained consisting of 23.3% (w/w) D-pantothenate, <0.1% chloride, 0.67% sulfate and <0.01% phosphate. Cations included 17.2% calcium (97% of all cations detected), 0.2% sodium, <0.1% ammonium, <0.1% potassium and <0.1% magnesium.

EXAMPLE 4

Amberlite IRA 958; Elution with 20% Acetic Acid

The strongly basic anion exchange resin Amberlite IRA 958 (600 mL) was loaded with 1453 mL of the pasteurized and ultrafiltrated bio-broth obtained according to Example 1. The flow rate was regulated to 1 L/h. Using the same flow rate, the column was washed with 606 mL of demineralized water. Then the pantothenate was eluted with a flow rate of 1 L/h using 1000 mL of acetic acid (20%). 781 mL of eluate were collected. The column was regenerated with demineralized water (773 mL), 4% aqueous NaOH solution (1200 mL) and again demineralized water (1000 mL).

The eluate was concentrated on a rotary evaporator at reduced pressure and a temperature in the range of 50-70° C.

The concentrated crude product was diluted with water (1:1) and then 9.53 g of $Ca(OH)_2$ (as a 25% suspension in water) were added to adjust the pH value to 7. The solution was concentrated and dried on a rotary evaporator. 52.40 g of free-flowing yellow product were obtained consisting of 40.8% (w/w) D-pantothenate, <0.1% chloride, 0.15% sulfate and <0.01% phosphate. Cations include 9.3% calcium (91% of all cations detected), 0.1% sodium, 0.6% ammonium, <0.1% potassium and <0.1% magnesium.

The invention claimed is:

1. A process for preparation of calcium-D-pantothenate comprising isolating and purifying it from a fermentation broth of a pantothenic acid producing microorganism, comprising:
   (a) eluting D-pantothenic acid from a strongly basic anion exchange resin with an aqueous solution of 10-20% (w/w) acetic acid,
   (b) neutralizing the eluate by addition of a basic calcium salt, and
   (c) transferring the neutralized solution into a free-flowing product capable of being used as an animal feed supplement.

2. The process as claimed in claim 1, wherein neutralization of the eluate from the anion exchange resin is effected with calcium hydroxide or calcium carbonate.

3. The process as claimed in claim 1 further comprising: treating the fermentation broth with charcoal.

4. The process as claimed in claim 1 further comprising: treating the neutralized solution with charcoal.

5. A process for preparation of calcium-D-pantothenate comprising:
   (a) binding D-pantothenic acid from a fermentation broth to a strongly basic anion exchange resin,
   (b) eluting D-pantothenic acid from the strongly basic anion exchange resin with an aqueous solution of 10-20% (w/w) acetic acid,
   (c) neutralizing the eluate with a basic calcium salt to a pH of 6-8, and
   (d) obtaining a free-flowing product comprised of calcium-D-pantothenate from the neutralized solution.

6. The process according to claim 5, wherein neutralization of the eluate from the anion exchange resin is effected with calcium hydroxide or calcium carbonate.

7. The process according to claim 5 further comprising: treating the fermentation broth with charcoal before loading.

8. The process according to claim 5 further comprising: treating the eluate with charcoal after neutralization.

9. The process according to claim 5 further comprising: removing acetic acid from the eluate by distillation.

10. The process according to claim 5, wherein the free-flowing product is obtained by spray drying.

11. The process according to claim 5, wherein the free-flowing product is obtained by spray granulation.

12. The process according to claim 5, wherein the free-flowing product is obtained using a rotary evaporator.

* * * * *